United States Patent [19]

Mendez

[11] 4,428,746
[45] Jan. 31, 1984

[54] GLAUCOMA TREATMENT DEVICE

[76] Inventor: Antonio Mendez, P.O. Box 925, Calexico, Calif. 92231

[21] Appl. No.: 288,150

[22] Filed: Jul. 29, 1981

[51] Int. Cl.$^3$ ............................................. A61M 5/00
[52] U.S. Cl. ........................................ 604/8; 604/48; 604/49; 604/93; 128/20
[58] Field of Search ............... 24/230.5 AD, 230.5 W, 24/261 R; 3/1.5, 13; 128/1 R, 350 R, 303 R, 20, 128/130, 275; 604/48, 49, 8, 93

[56] References Cited

U.S. PATENT DOCUMENTS

| | | | |
|---|---|---|---|
| 1,280,979 | 10/1918 | Ellis | 128/130 |
| 2,834,023 | 5/1958 | Leib | 3/13 |
| 3,159,161 | 12/1964 | Ness | 128/350 R |
| 4,321,916 | 3/1982 | McKoe | 128/20 |
| 4,327,450 | 5/1982 | Girard | 3/13 |

FOREIGN PATENT DOCUMENTS 114051 3/1918 United Kingdom .

OTHER PUBLICATIONS

Lancet, Jan. 1952, "Intra-Ocular Acrylic Lenses After Cataract Extraction."

*Primary Examiner*—C. Fred Rosenbaum
*Assistant Examiner*—J. L. Kruter
*Attorney, Agent, or Firm*—Hugh D. Jaeger

[57] ABSTRACT

Glaucoma treatment device for surgical implant for the treatment and management of glaucoma. The glaucoma treatment device includes a single continuous length of cylindrical member having two ends substantially in a first plane and angled slightly inwards toward each other, two smaller loops having the small loops substantially in a like second plane at a slight outward angle to the first plane and each outer end of the small loops connected to the two ends, and an elongated large loop with a large end radius in between the two ends, substantially positioned in the first plane and connected to the inner ends of the smaller loops. The cylindrical member can consist of polymethylmethacrylate or like material. The device is surgically implanted in the eye under a partial thickness scleral flap in the newly formed scleral bed, and secures a channel for aqueous humor to flow away from the eye.

14 Claims, 13 Drawing Figures

GLAUCOMA TREATMENT DEVICE

BACKGROUND OF THE INVENTION

1. Field of the Invention

The present invention relates to a surgically implantable ophthalmologic treatment device and, more particularly, pertains to a surgical implant glaucoma treatment device for management and treatment of glaucoma.

2. Description of the Prior Art

The prior art has provided drugs, surgical procedures and devices for the management and treatment of glaucoma.

One treatment of glaucoma involves eye drops to the individual, daily or before retiring, which tends to decrease intraocular pressure. However, in some cases intended benefits do not materialize or the medications become too expensive.

Surgical procedures for treatment of glaucoma can include the trabeculotomy, thermal sclerotomy, Schie (thermal sclerotomy) method or the trabeculectomy, all of which are intended to relieve intraocular pressure.

Another more recent method for the control of glaucoma is referred to as the Storz Krupin-Denver eye valve which is an open tube extending 1 to 4 millimeters into the anterior chamber. A silicone tube attaches to the open tube at an angle where the sealed end of the silicone tube contains horizontal and vertical slits to control aqueous drainage to subscleral space. Two side-arms are sutured to the sclera providing stability. The valve flow rate increases as the intraocular pressure increases. The particular problem with this type of valvular device for controlling glaucoma within glaucomatous eyes is that the eye valve can become clogged, no longer passing fluid and allowing the intraocular pressure (I.O.P.) to increase, resulting in the same preoperative condition. Also, the eye valve may require supportive medical therapy. This type of eye valve is described in U.S. Pat. No. 4,037,604.

The present invention overcomes the disadvantages of the prior art by providing a glaucoma treatment device for surgical implant which is a single continuous length cylindrical member providing for a channel and pathway for aqueous humor to leave the eye, thereby providing long-term management and treatment of glaucoma.

The present invention is utilized in a surgical operation which is similar to types of surgical maneuvers familiar to the surgeon. The present invention includes the surgical implantation of the glaucoma treatment device which offers distinct benefits over other implantable devices or valves and provides for long-term management and treatment which is absent in the prior art.

SUMMARY OF THE INVENTION

The general purpose of the present invention is to provide a glaucoma treatment device for surgical implant in the management and treatment of glaucoma, and which provides for long-term high reliability of treatment in a patient. The implantable device is surgically implanted into the anterior chamber of the eye under at least a partial scleral flap, thereby providing a channel for aqueous humor to flow away from the eye and thereby relieve pressure on the eye. The implantable glaucoma treatment device provides for long-term treatment.

According to one embodiment of the present invention, there is provided a surgically implantable glaucoma treatment device for treatment and management of glaucoma, the glaucoma treatment device comprising a single continuous length of cylindrical member of polymethylmethacrylate or the like material having two ends substantially in a first plane, aligned and angled slightly inwards toward each other, two smaller loops having the loops substantially in a like second plane at a slight outward angle to the first plane and each outer end of the small loops connected to the two ends, and an elongated large loop having a major radius in between the two ends, substantially in the first plane and connected to the inner ends of the smaller loops where the connection between the small loops and the elongated large loop and two ends form a third plane where the third plane is at an angle of less than 90° with respect to the first or second planes, thereby providing a glaucoma treatment device which is surgically implanted into the anterior chamber and under a scleral flap or partial scleral flap of an eye, thereby securing a channel for discharge of aqueous humor to flow away from the eye for decrease of intraocular pressure.

According to another embodiment of the present invention, there can be provided a glaucoma treatment device having two ends in a first plane, a small loop in a second plane, and connecting members in a third plane whereby the third plane is at an angle with respect to the first and second planes.

According to an additional embodiment of the present invention, there is provided a glaucoma treatment device having two ends in a first plane, three smaller loops in a second plane, two large loops in the first plane and positioned between the two ends, and connecting members connecting the three small loops to the two large loops and the two ends whereby the third plane is at an angle with respect to the first and second planes.

A significant aspect and feature of the present invention is a glaucoma treatment device, now known in ophthalmology as a Mendez Seton glaucoma treatment device for the long-term treatment and long-term management of glaucoma, which device is surgically implantable to provide for a channel for discharge of aqueous humor. The device is substantially a three-plane member of non-biodegradable synthetic material providing a flexible pathway and channel for the discharge of aqueous humor from the eye, and thereby reducing intraocular pressure in the eye.

Another significant aspect and feature of the present invention is a glaucoma treatment device which can be surgically implanted in a process which does not involve complex, tedious surgery. In a typical procedure, the surgery involves creating a partial scleral flap, lifting the flap, slitting the flap, creating a longitudinal incision into the anterior chamber and anterior to the iris inserting the implantable glaucoma treatment device with the smaller loops substantially passing over the canal of schlemm through the trabecular meshwork and over the sclera, suturing the top of the large loop between the sclera, suturing the flaps, and reconstituting the anterior chamber through the injection of air. Also, a section of the canal of Schlemm and/or trabecular meshwork may be removed at the discretion of the surgeon and/or because of anatomical considerations discovered by the surgeon either preoperatively or intraoperatively.

A further significant aspect and feature of the present invention is a glaucoma treatment device having a preformed geometrical shape of a cylindrical member of a finite continuous length which is implanted in the eye. The member is made of a solid material which is compatible with the eye and creates a channel. The material is flexible, soft to the touch, and does not plug up as is common with many prior art devices.

An additional significant aspect and feature of the present invention is a glaucoma treatment device which is inserted partially into the anterior chamber of the eye, is of nonbiogradable material, utilizes synthetic material for long-term treatment, and provides and secures a track for continuous channeled discharge of aqueous humor. The particular type of material, polymethylmethacrylate, is a material which does not encourage invasive growth of tissue. However, other synthetic materials could be used.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
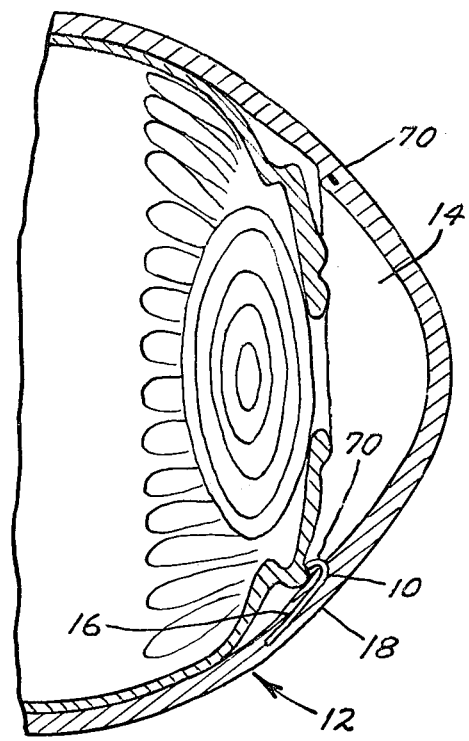
FIG. 1 illustrates a glaucoma treatment device surgically implanted in the eye.

FIG. 1, which illustrates a side view of a glaucoma treatment device 10, shows the treatment device 10 surgically implanted into an eye 12 and extending into the anterior chamber 14. The glaucoma treatment device 10 positions under a scleral flap or partial scleral flap 18 adjacent the tenon membrane 16, and extends into the anterior chamber 14 of the eye 12. The process for surgical implantation is described in later detail in the mode of operation.

Figure 2:
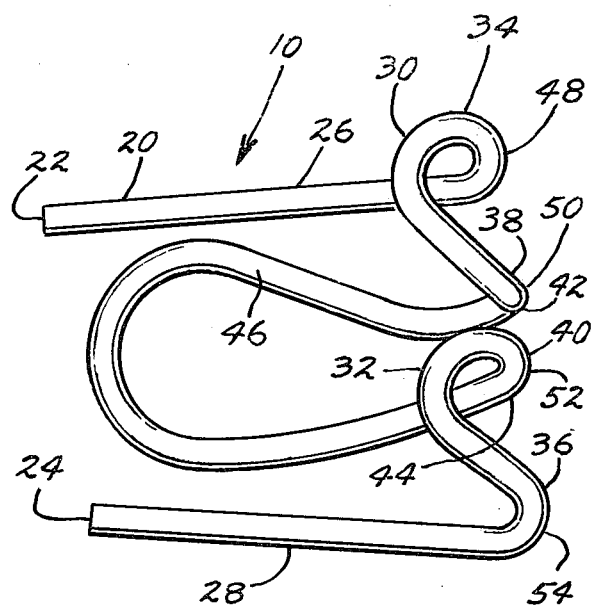
FIG. 2 illustrates a perspective view of the glaucoma treatment device.

FIG. 2, which illustrates a perspective view of the glaucoma treatment device 10, shows a cylindrical member of a finite continuous length 20 and a diameter in the range of 0.01 mm to 5 mm, preferably 0.25 mm. The cylindrical member can consist of a synthetic material such as polymethylmethacrylate, hereinafter referred to as PMMA, a term of the art, by way of example and for purposes of illustration only, or a like material. The member 20 includes two ends 22 and 24, two longitudinally extending and outwardly angled members 26 and 28, and two small loops 30 and 32 having outer ends 34 and 36 connected to opposing ends 38 and 40 of the member 20. Inner ends 38 and 40 of the small loops 30 and 32 respectively connect to ends 42 and 44 of an elongated large loop 46 having a major radius in the member 20. The large loop 46 is in substantially a first plane as all the outwardly extending members 26 and 28. The small loops 30 and 32 are substantially in the same plane, referenced as a second plane. The joining of the ends of the small loops 30 and 32 to the ends of the extending members 26 and 28 and the large loop 46 with curvature segments 48, 50, 52 and 54 form a third plane at the tangent to the curved segments 48-54. The angle between the first plane and second plane is less than 90°. The angle of the third plane to either the first or second plane is less than 90°.

Figure 3:
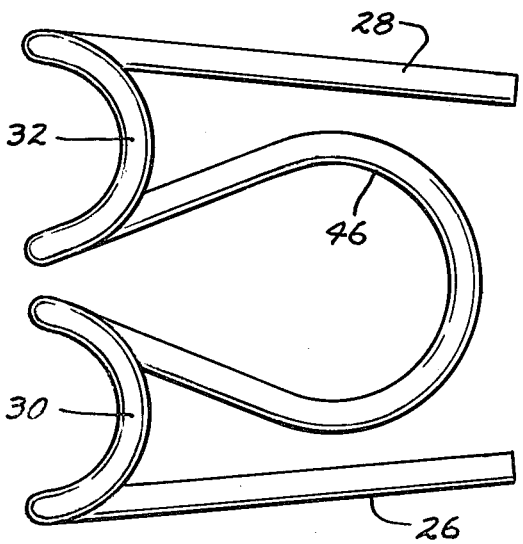
FIG. 3 illustrates a bottom view of the glaucoma treatment device.

FIG. 3, which illustrates a bottom view of the glaucoma treatment device 10, shows the large loop 46, and the small loops 30 and 32. All other numerals correspond to those elements previously described. The extending members 26 and 28 and the large loop 46 position in the area of the scleral flap. The large loop 46 is secured with a suture, as later described in detail. The small loops 30 and 32 position into the anterior chamber of the eye.

Figure 4:
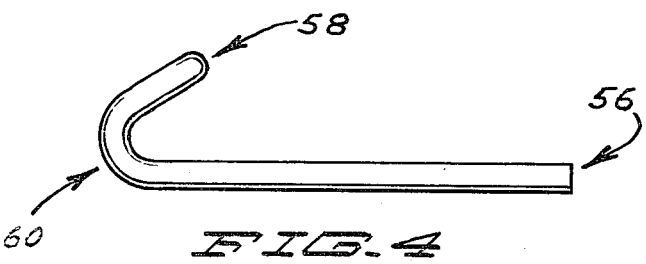
FIG. 4 illustrates a side view of the glaucoma treatment device.

FIG. 4, which illustrates a side view of the glaucoma treatment device 10, shows the first plane 56, the second plane 58 and the third tangential plane 60 where the first plane 56 engages under the scleral flap or partial scleral flap, the third plane 60 positions into the anterior chamber of the eye and the second plane 58 loops over the area of the canal of schlemm and trabecular meshwork if these anatomical parts are not removed during surgery.

Figure 5:
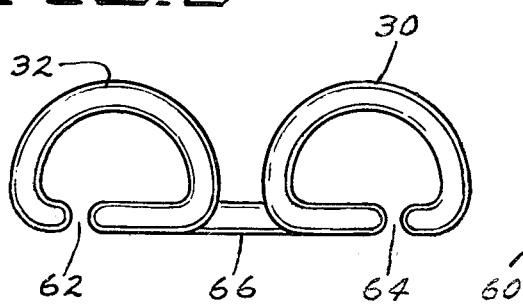
FIG. 5 illustrates an end view of the glaucoma treatment device.

FIG. 5, which illustrates an end view of the glaucoma treatment device 10, shows the small loops 30 and 32, and the large loop 46. Geometrical spaces 62 and 64 correspond to the spacing between the elongated large loop 46 and the members 26 and 28. Geometrical space 66 is provided by the ends 42 and 44, the large elongated loop 46 narrowing at the connection to the ends 38 and 40.

PREFERRED MODE OF OPERATION

The glaucoma treatment device 10 can be implanted by known ophthalmological surgical procedures. After the patient is diagnosed as having glaucoma and it is determined that the glaucoma treatment device 10 is the preferred treatment and management procedure, the patient is prepared for surgery and anaesthetized either with local or general anaesthesia.

Figure 6A:
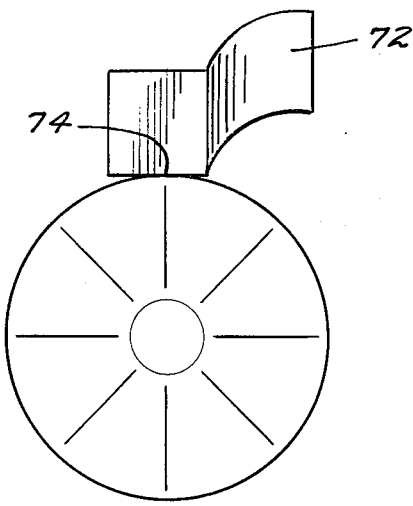
FIGS. 6A-6F illustrate steps for a surgical procedure for implant of the glaucoma treatment device.
Figure 6B:
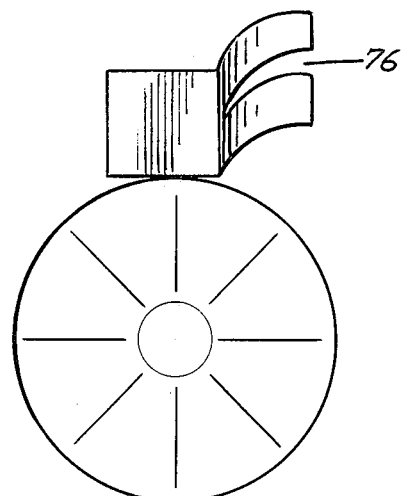
Figure 6C:
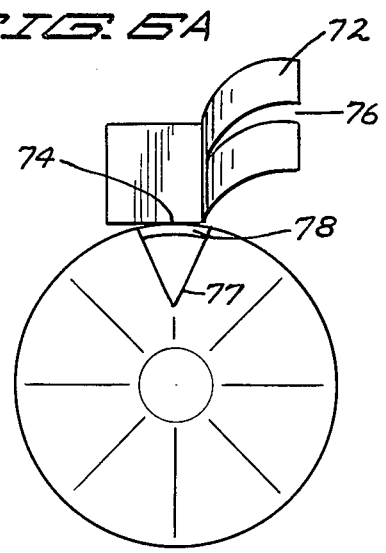

FIGS. 6A-6F illustrate a surgical implant procedure generally involving six steps. FIG. 6A, the first step, is to create a scleral flap or partial scleral flap 72 at the limbus 74 which hinged portion thereof is vertical but can also be horizontal and parallel with the limbus. FIG. 6B, the second step, is to slit (76) the flap. FIG. 6C, the third step, is to create a slit 78 into the anterior chamber of the eye and may be at the discretion of the surgeon to remove a section of the canal of Schlemm and/or to remove a portion of the trabecular meshwork providing for access to the anterior chamber of the eye as in the trabeculectomy procedure. An irredectomy procedure 77 can also be utilized.

Figure 6D:
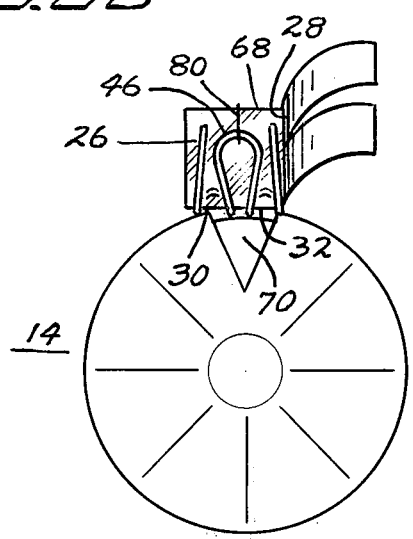

FIG. 6D illustrates the surgical implant of the glaucoma treatment device 10, the fourth step, where the device 10 is positioned such that the small loops 30 and 32 extend into the anterior chamber 14 of the eye 12 about the area of the canal of schlemm 68 and the trabecular meshwork 70 whether or not either has been removed. The elongated large loop 46 and the members 26 and 28 can engage between the surfaces of the canal of schlemm 68 and the trabecular meshwork 70 or in the immediate area thereof. The small loops 30 and 32 protrude into the anterior chamber 14 of the eye 12. The three loops 30, 32 and 46 respectively with the other connecting structure provide a channel for the aqueous humor to discharge and flow from the interior of the eye.

The glaucoma treatment device 10 provides that the edges of the scleral flap about the area of the canal of schlemm 68 and trabecular meshwork 70 are maintained in a somewhat spaced relationship allowing for aqueous humor to discharge along, in between, and around the channels provided by the predetermined geometrical shape of the treatment device 10, and about the channels maintained and provided by the small loops 30 and 32 and the channels provided by the large loop 46.

The glaucoma treatment device 10 forms a channel providing a pathway for the discharge of aqueous humor to leave the eye by a means other than the normal primary pathway which is the canal of schlemm. The synthetic material, in this instance polymethyl-methacrylate, of the glaucoma treatment device by virtue of the design and method of manufacture provides a smooth, flexible device which is securely positioned at implantation which enhances the operation in the management and treatment of glaucoma and is deformable with the eye. The device 10 or implant, due to its light weight and the predetermined geometrical loop structure, is not noticeable to the individual patient and is barely perceptible to the touch. FIG. 6D shows the glaucoma treatment device 10 sutured into position at the end of the elongated large loop 46 to the sclera 68 with a suture 80.

Figure 6E:
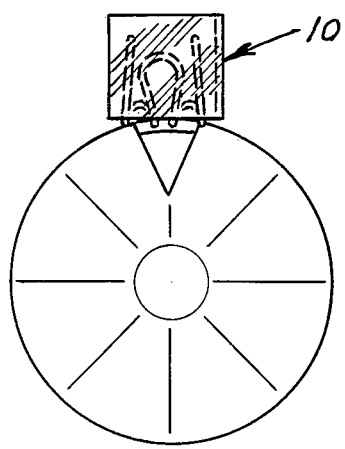

FIG. 6E illustrates positioning and securing of the glaucoma treatment device 10 where the members of the split scleral flap 18 are sutured down across the extending members 26 and 28 and over the large loop 46 with a plurality of sutures, usually two to four.

Figure 6F:
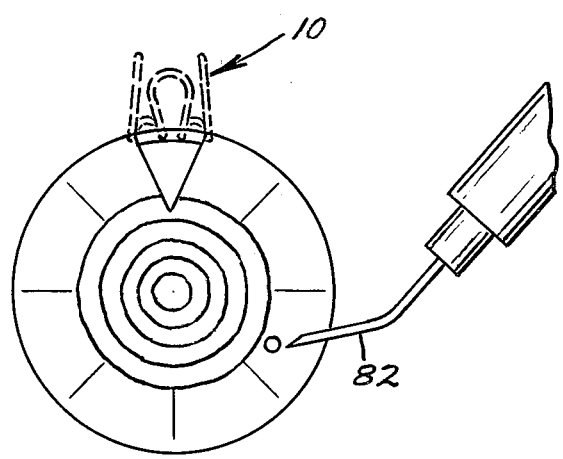

FIG. 6F illustrates that after the eye has been surgically closed, the anterior chamber of the eye is reconstituted with air 82.

Depending upon the surgical procedure, it is foreseeable that the surgeon could implant the glaucoma treatment device by piercing the anterior chamber and implanting the device only, doing a combined procedure, implant and trabeculectomy including irridectomy 77.

Also, in the alternative, a vertical dissection of the scleral flap can be surgically performed at a 90° angle to the limbus, resulting in a hinge at a 90° angle to the limbus in lieu of a horizontal dissection at the limbus.

By way of example and for purposes of illustration only, the glaucoma treatment device can have dimensions such as 3.5 mm wide at outward extending members 26 and 28, 3 mm in length for height of the extending members, and 1 mm in length for height of the small loops 30 and 32. The dimensions are not to be construed as limiting of the present invention.

ALTERNATIVE EMBODIMENTS

Figure 7:
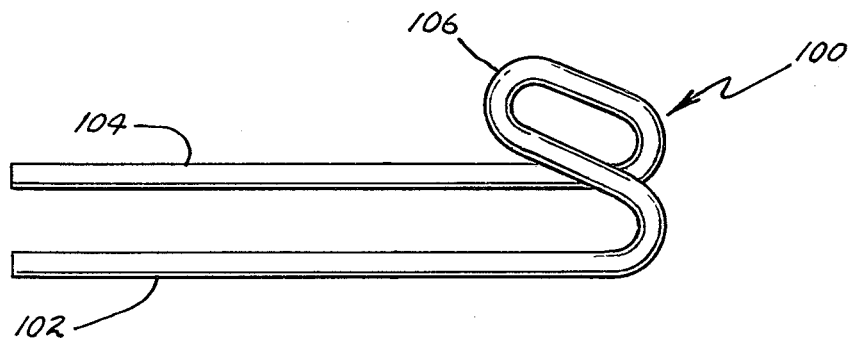
FIG. 7 illustrates another embodiment of a glaucoma treatment device.

FIG. 7, which illustrates another embodiment of a glaucoma treatment device having only one small loop, shows a glaucoma treatment device 100 having two extending members 102 and 104 and a small loop 106. Structure and operation is similar to that previously described. The device 100 is smaller in width than that of device 10 in having one fewer small loop and absent the large loop.

Figure 8:
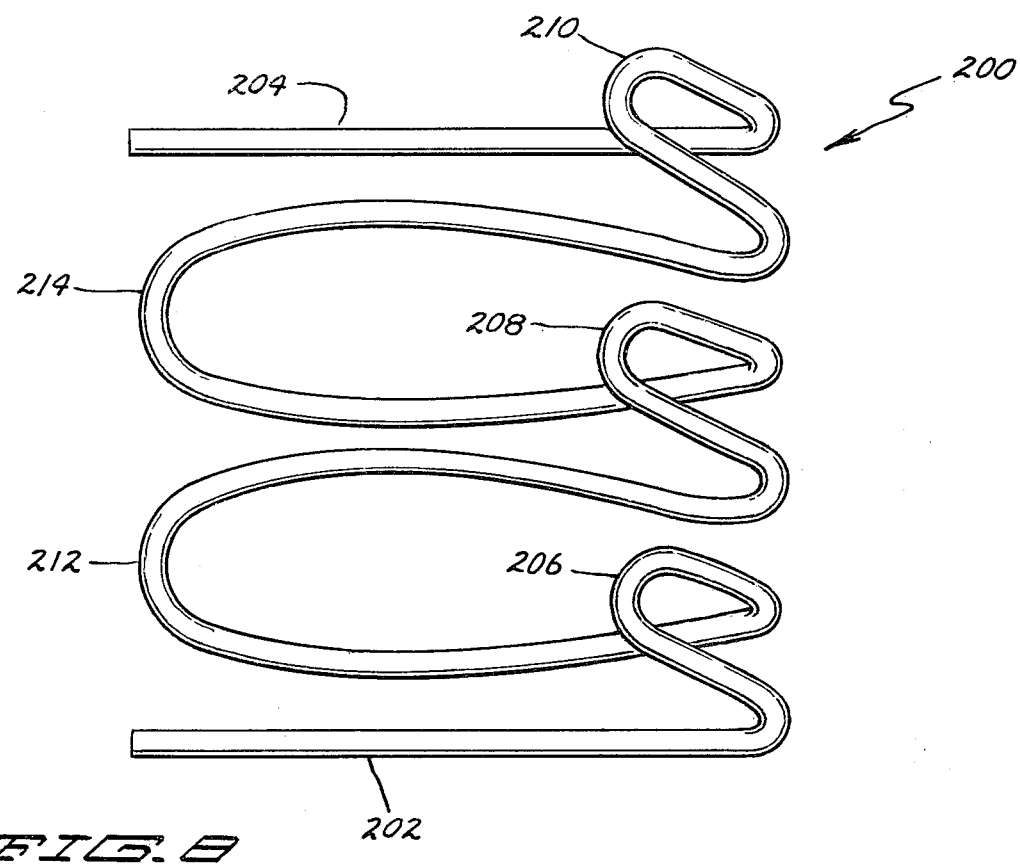
FIG. 8 illustrates an additional embodiment of a glaucoma treatment device.

FIG. 8, which illustrates an additional embodiment of a glaucoma treatment device having two large elongated loops and three small loops disposed therebetween, shows a glaucoma treatment device 200 having two extending members 202 and 204, three small loops 206, 208 and 210, and two large loops 212 and 214. Structure and operation are similar to that previously described. The device 200 is larger in width than that of device 10 in having one additional small and large loop.

Other embodiments are within the apparent scope of the present invention without departing from the disclosure of the specification. Other predetermined geometrical shapes can accomplish the same result with like geometrical structures of predetermined shapes. While the glaucoma treatment devices have illustrated an elongated circle and loops, other geometrical configurations such as circles, ovoids, parabolas, and ellipses of the cylindrical member can be utilized. The elongated large loop can assume another like predetermined, geometrical shape than that disclosed. The small loop or loops can assume any other geometrical shapes than those disclosed, whether the shapes are identical or different. Likewise, the analogy applies to all the figures. The continuous cylindrical member while being disclosed as being solid can also be tubular. The cylindrical member itself can assume other predetermined geometrical cross sections such as ovoid, square, rectangular, eliptical, or other predetermined geometrical cross section. The geometrical cross section can vary over the length of the cylindrical member. Any suitable type of synthetic or like material could also be used to form the cylindrical member, although the cylindrical member could assume any other predetermined geometrical configuration. The length and width of the glaucoma treatment devices is determined by the particular geometrical configuration or geometrical configurations. The synthetic material is such a type as being deformable and flexible to the touch and normal physical movements, but maintaining a predetermined geometrical shape through memory of that predetermined geometrical shape.

What is claimed is:

1. Glaucoma treatment device for treating disease of glaucoma in the human eye by surgical implant, said device comprising:
   a. means including at least two small geometrical loop means of a small diameter and a large slightly elongated loop in a plane with said two small loop means and connected to said ends of said small loops for positioning within a portion of the eye; and,
   b. means including two substantially aligned parallel members connected to said loop means at an angle for positioning in at least a partial scleral flap of said eye, and connected at an angle to said loop means whereby said device provides a canal between said loop means and said member means thereby providing for discharge of aqueous humor from interior of said eye.

2. Glaucoma treatment device of claim 1 wherein said loop means comprises three small loop means connected to each other and large slightly elongated loops in a plane with said small loop means and connected to ends of said small loops.

3. Glaucoma treatment device of claim 2 wherein comprising two large slightly elongated loops in a plane with said members and connected to ends of small loop means.

4. Glaucoma treatment device of claim 1 wherein said loop means comprise a continuous cylindrical member of continuous length forming said loop means and said members.

5. Glaucoma treatment device of claim 4 wherein said cylindrical member is polymethylmethacrylate.

6. Glaucoma treatment device of claim 5 wherein said cylindrical member is of a diameter in the range of 0.01 to 5.0 millimeters.

7. Glaucoma treatment device of claim 5 wherein said cylindrical member is substantially of a diameter of 0.25 mm.

8. Glaucoma treatment device of claim 5 wherein said loop means substantially are of a height of 1 mm and said member means are substantially of a height of 3 mm and a width of 3.5 mm.

9. Glaucoma treatment device of claim 1 wherein said loop means are at an angle to said member means in the range of less than ninety degrees.

10. Glaucoma treatment device of claim 1 comprising a third means connecting said first means to said second means.

11. Glaucoma treatment device of claim 1 wherein said loop means and said member means consist of flexible polymethylmethacrylate material.

12. Glaucoma treatment device for surgical implant in an eye, said device comprising:
  a. at least two small loop means on one plane providing a discharge channel from an anterior chamber of said eye; and,
  b. at least one large loop means connecting between said two small loop means and two member means connected to outer ends of said small loop means providing channels for surfacing within sclera of said eye whereby said discharge channel means and said channel surface member means provide for discharge of aqueous humor from an anterior chamber of said eye.

13. Glaucoma treatment device comprising:
  a. continuous finite length of a geometrical member, said member including a substantially identical geometrical cross section at each increment of said finite length including two ends in a first plane;
  b. at least two small loop means in a second plane at an angle to said first plane and each outer end of said loop means connected to said ends; and,
  c. at least one elongated large loop including a major radius in said first plane and connected between each of said small loop means whereby said small loop means are surgically implanted into an anterior chamber of an eye and said large loop and ends are under a scleral flap or partial scleral flap of said eye thereby securing a channel for discharge of aqueous humor to flow away from said eye for decrease of pressure.

14. Process for management and treatment of glaucoma in an eye with a glaucoma treatment device, said process comprising:
  a. dissecting tissue down a plane at corneo-sclera limbus forming a scleral flap slightly larger than a surface channel of an elongated large loop and extending members of said glaucoma treatment device;
  b. slitting said flap substantially in center with a narrow slit for engagement over said extending members and elongated large loop of said device;
  c. sectioning out a portion of said eye for accepting small loops which protrude into anterior chamber of said eye;
  d. positioning the glaucoma treatment device between the scleral flap with the small loops extending into the anterior chamber of the eye and the elongated large loop and extending members positioned in said sclera;
  e. suturing the surface portion of the glaucoma treatment device to at least one point to said sclera;
  f. suturing said scleral flaps over the surface portion of said device; and,
  g. reconstituting the anterior chamber of the eye with air whereby the glaucoma treatment device is surgically implanted into the anterior chamber thereby securing a channel for aqueous fluid to discharge from the eye in management and treatment of glaucoma.

* * * * *